United States Patent
Lin et al.

(10) Patent No.: US 10,188,542 B2
(45) Date of Patent: Jan. 29, 2019

(54) COMPLETE FLOW DIVERSION INTESTINAL OSTOMY SURGERY KIT

(71) Applicants: Jianjiang Lin, Hangzhou, Zhejiang (CN); Hanju Hua, Hangzhou, Zhejiang (CN)

(72) Inventors: Jianjiang Lin, Hangzhou (CN); Hanju Hua, Hangzhou (CN); Jiahe Xu, Hangzhou (CN)

(73) Assignees: Jianjiang Lin, Hangzhou (CN); Hanju Hua, Hangzhou (CN)

( * ) Notice: Subject to any disclaimer, the term of this patent is extended or adjusted under 35 U.S.C. 154(b) by 543 days.

(21) Appl. No.: 14/911,249

(22) PCT Filed: Aug. 23, 2014

(86) PCT No.: PCT/IB2014/064032
§ 371 (c)(1),
(2) Date: Feb. 9, 2016

(87) PCT Pub. No.: WO2015/028926
PCT Pub. Date: Mar. 5, 2015

(65) Prior Publication Data
US 2016/0193072 A1 Jul. 7, 2016

(30) Foreign Application Priority Data
Aug. 27, 2013 (CN) .......................... 2013 1 0379014

(51) Int. Cl.
*A61F 5/44* (2006.01)
*A61F 5/445* (2006.01)

(52) U.S. Cl.
CPC ............ *A61F 5/4405* (2013.01); *A61F 5/445* (2013.01)

(58) Field of Classification Search
CPC combination set(s) only.
See application file for complete search history.

(56) References Cited

U.S. PATENT DOCUMENTS 4,555,242 A * 11/1985 Saudagar ................ A61F 5/445
604/103.08
4,634,421 A * 1/1987 Hegemann ............ A61F 2/0009
251/7

(Continued)

FOREIGN PATENT DOCUMENTS

CN 2774430 Y 4/2006
CN 200954264 Y 10/2007
(Continued)

OTHER PUBLICATIONS

International Search Report, issued in PCT/IB2014/064032, dated Dec. 15, 2014.

*Primary Examiner* — Tatyana Zalukaeva
*Assistant Examiner* — Guy K Townsend
(74) *Attorney, Agent, or Firm* — Birch, Stewart, Kolasch & Birch, LLP

(57) ABSTRACT

A complete flow diversion intestinal ostomy surgery kit, comprising an ostomy tube, the ostomy tube comprising a tube body; near the front end of the tube body is provided with a deformable balloon; a fine tube is provided within the tube wall of the tube body or inside the tube body; the front end of the fine tube penetrates the tube wall of the tube body and is in communication with the inner cavity of the balloon; when filled with fluid via a connector, the balloon and the intestinal wall form a sealed structure that blocks matters inside of the intestine; the complete flow diversion intestinal ostomy surgery kit further comprises a ring-shaped fixing plate; the exterior wall of the tube body is provided with a ring-shaped groove; the ostomy tube is fixedly connected to the abdominal wall of a patient via the ring-shaped fixing plate that matches the ring-shaped groove. By controlling the pressure of the balloon to divert the flow of matters inside of the intestine, the matters inside of the intestine is guided out via the ostomy tube. When the anastomosis at the far end is healed, the ostomy tube is pulled out and removed, and the anastomosis automatically closes.

8 Claims, 4 Drawing Sheets

(56) References Cited

U.S. PATENT DOCUMENTS

| | | | | |
|---|---|---|---|---|
| 4,662,890 A * | 5/1987 | Burton | | A61F 5/445 128/899 |
| 4,721,508 A * | 1/1988 | Burton | | A61F 5/445 604/103.03 |
| 4,863,438 A * | 9/1989 | Gauderer | | A61M 39/0247 604/247 |
| 4,872,483 A * | 10/1989 | Shah | | A61M 16/044 137/557 |
| 5,218,970 A * | 6/1993 | Turnbull | | A61B 5/03 128/207.15 |
| 5,860,960 A * | 1/1999 | Quinn | | A61J 15/0015 604/174 |
| 5,891,113 A | 4/1999 | Quinn | | |
| 6,039,714 A * | 3/2000 | Cracauer | | A61J 15/0034 604/103.03 |
| 6,066,112 A * | 5/2000 | Quinn | | A61J 15/0015 604/174 |
| 6,077,243 A * | 6/2000 | Quinn | | A61J 15/0015 128/DIG. 26 |
| 6,332,877 B1 * | 12/2001 | Michels | | A61L 29/043 604/263 |
| 6,485,476 B1 * | 11/2002 | von Dyck | | A61F 5/441 600/29 |
| 6,595,971 B1 * | 7/2003 | von Dyck | | A61F 5/442 604/334 |
| 7,124,489 B2 * | 10/2006 | Triebes | | A61M 25/001 29/428 |
| D561,329 S * | 2/2008 | McMichael | | A61M 5/445 D24/108 |
| 7,582,072 B2 * | 9/2009 | McMichael | | A61J 15/0057 604/174 |
| 8,801,683 B2 * | 8/2014 | Kim | | A61M 3/0241 600/29 |
| 9,125,800 B2 * | 9/2015 | Baker | | A61B 17/3415 |
| 2002/0077611 A1 * | 6/2002 | von Dyck | | A61F 5/442 604/333 |
| 2003/0225376 A1 * | 12/2003 | Fournie | | A61J 15/0015 604/175 |
| 2004/0024363 A1 * | 2/2004 | Goldberg | | A61J 15/0015 604/175 |
| 2007/0088280 A1 * | 4/2007 | Gomez | | A61M 25/02 604/174 |
| 2008/0091146 A1 * | 4/2008 | Solovay | | A61F 5/003 604/174 |
| 2009/0275795 A1 * | 11/2009 | Martino | | A61F 5/445 600/32 |
| 2010/0222802 A1 * | 9/2010 | Gillespie, Jr. | | A61B 90/02 606/192 |
| 2011/0040231 A1 * | 2/2011 | Gregory | | A61F 5/445 604/8 |
| 2011/0106032 A1 * | 5/2011 | Kratky | | A61F 5/445 604/337 |
| 2011/0295236 A1 * | 12/2011 | Gregory | | A61M 3/0295 604/540 |
| 2013/0079712 A1 * | 3/2013 | Bagwell | | A61J 15/0069 604/96.01 |
| 2017/0197028 A1 * | 7/2017 | Goldsmith | | A61M 5/158 |
| 2017/0367932 A1 * | 12/2017 | Millis | | A61J 15/0015 |

FOREIGN PATENT DOCUMENTS

| | | |
|---|---|---|
| CN | 201551719 U | 8/2010 |
| CN | 202590135 U | 12/2012 |
| CN | 103405297 A | 11/2013 |
| CN | 203468829 U | 3/2014 |
| CN | 104146809 A | 11/2014 |

* cited by examiner

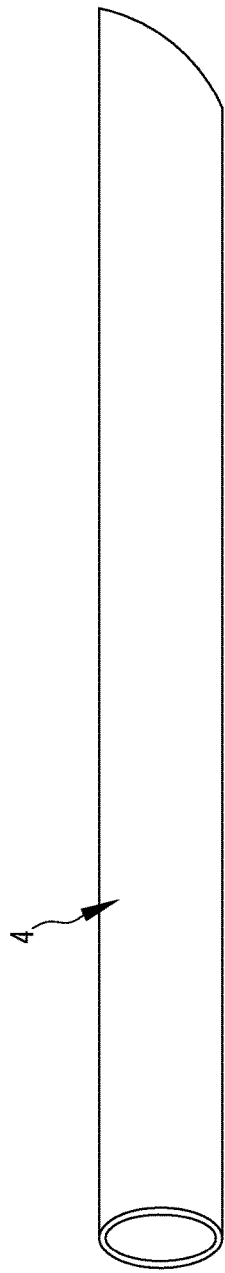
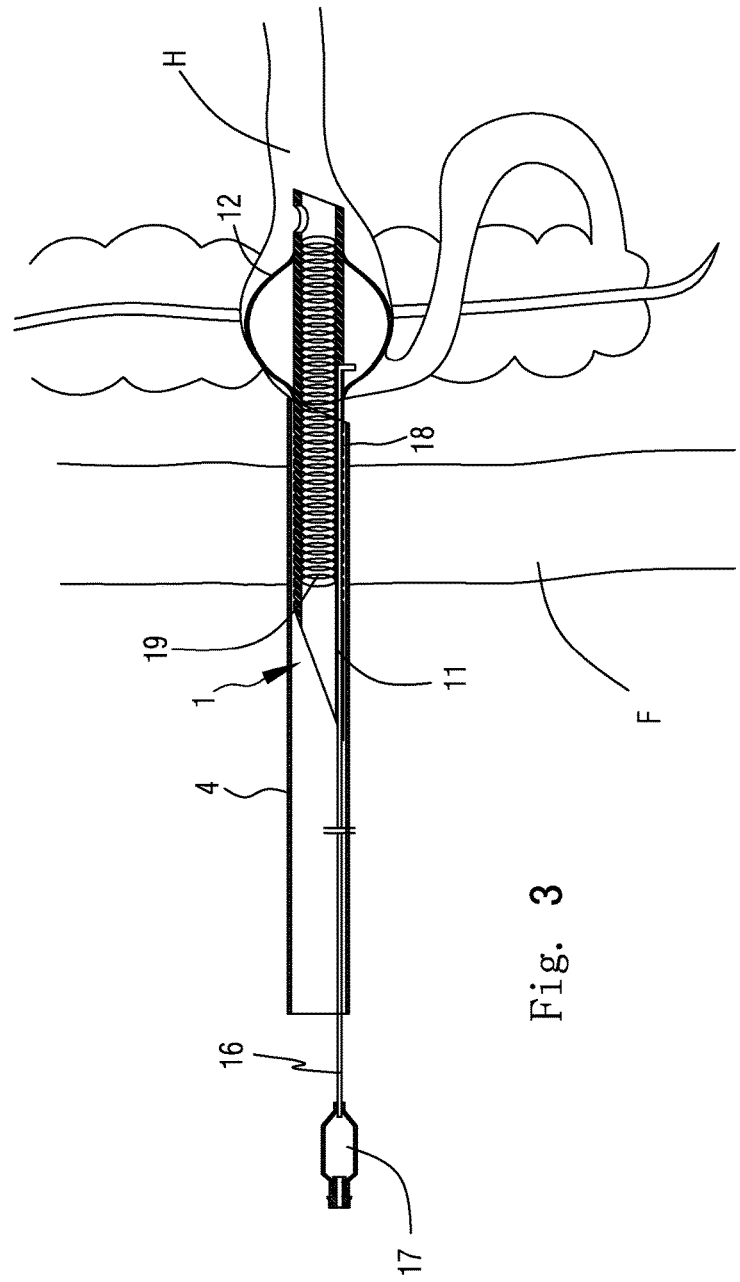
Fig. 2
Fig. 3

COMPLETE FLOW DIVERSION INTESTINAL OSTOMY SURGERY KIT

FIELD OF THE INVENTION

The present application relies on and claims priority of Chinese patent application 201310379014.4 filed on Aug. 27, 2013, hereafter combines all the content of the above priority into present application for reference. The present invention relates to a complete flow diversion intestinal ostomy surgery kit.

BACKGROUND OF THE INVENTION

The risk of anastomosis leakage following low-order rectal cancer resection brings severe surgical complication. Temporary protective ileostomy decreases the risk of anastomosis leakage and the complication caused. However, regular second ileostomy closing operation need to close the anastomosis twice and may also cause anastomosis leakage and intestinal obstruction. How to avoid the second ileostomy closing and the potential complications afterwards is a challenge for anorectal surgeons.

Chinese patent application 201110343626.9 disclosed a temporary ileum ostomy tube. The ostomy tube was placed through the incision of the abdominal wall at the end of ileum. In the condition of negative pressure, the matters inside of the intestine were blocked to colon and were guided out. Instead of a second ileostomy closing, the ostomy tube can be pulled out and removed, and the intestinal wall will automatically close. However, the technical structure of the prior art is complex and the major defects of the prior art are tube obstruction and inconvenience of maintenance because the diameter of the ostomy tube was too small and thus requires negative pressure.

SUMMARY OF THE INVENTION

Technical Problems

To improve the existing ostomy tube in terms of its defects of long drainage distance, poor divert effect and complex structure, the present invention disclosed a complete flow diversion intestinal ostomy surgery kit, which has a better and controllable flow diversion effect, and meanwhile, the anastomosis can automatically close to avoid a second surgery. Moreover, the present invention contrives a special sinus closing tube to avoid the sinus closing failure after the removal of ostomy tube.

Technical Solution

In order to solve the above technical problems, the present invention disclosed a complete flow diversion intestinal ostomy surgery kit, comprising at least an ostomy tube, the said ostomy tube comprising a tube body; near the front end of the tube body is provided with a deformable balloon; the said tube body preceding the balloon forms a drainage section; a fine tube is provided within the tube wall of the said tube body or inside the said tube body; the front end of the fine tube penetrates the wall of the said tube body and is in communication with the inner cavity of the balloon; the rear end of the fine tube has a one-way valve connector for injecting fluid into the balloon with a one-way valve; the said connector is equipped with a manometer for measuring the pressure caused by the balloon impressed to the intestinal wall; after filled with fluid via the said connector the said balloon and the intestinal wall form a sealed structure that blocks matters inside of the intestine; there is a drainage port at the drainage section for guiding the matters inside of the intestine out through the said tube body; wherein the complete flow diversion intestinal ostomy surgery kit further comprises a ring-shaped fixing plate; the exterior wall of the tube body is provided with a ring-shaped groove; the said ostomy tube is fixedly connected to the abdominal wall of a patient via the ring-shaped fixing plate that matches the ring-shaped groove.

Preferably, the inner ring of the said ring-shaped fixing plate is provided with four jaws extending along the diameter of the said ring-shaped fixing plate, the space between the ends of the four jaws is slightly smaller than the outer diameter of the said tube body, the said ring-shaped fixing plate get stuck in the said ring-shaped groove by the way of pressing the said jaws.

Preferably, the said ring-shaped fixing plate is stuck on the upper or inner side of the stoma chassis.

Preferably, inner the said tube body has a pullable and pushable spring bracket.

Preferably, the said complete flow diversion intestinal ostomy surgery kit further comprises a sleeve placed at the rear end of the tube body matched therewith, for guiding the tube body out of the patient's abdominal wall.

Preferably, the said complete flow diversion intestinal ostomy surgery kit further comprises a sinus closing device, the said sinus closing device comprises a drainage tube and an outer fixing ring integrated therewith, the outside wall of the drainage tube has scale marks.

Preferably, the position where the outer fixing ring located is marked with zero scale, the scale marks on the drainage tubes on both sides of the said outer fixing ring are extended with millimeters.

Preferably, along the length direction of the drainage tube there are multiple side holes uniformly distributed.

Preferably, the exterior tube body of the said ostomy tube has scale marks.

Preferably, the said complete flow diversion intestinal ostomy surgery kit further comprises a sinus flushing device, which comprises a flushing tube with scale marks; the top side of the flushing tube has an aurilave.

Advantageous Effects

The complete flow diversion intestinal ostomy surgery kit of the present invention has following advantageous effects:

By controlling the specific balloon to block matters inside the intestine in present invention, matters inside the intestine can be guided out from the ostomy tube, which can provide temporary protection for the far end anastomosis. After the anastomotic at the far end heals, the ostomy tube can be removed and the anastomosis will close automatically, thus avoiding a second surgery.

Furthermore, in the present invention, the ostomy tube is stuck on the exterior abdominal wall by snap structure, preventing the tube body from retracting to the abdominal cavity, and avoiding suture to seize the tube body. It is easy to operate, without affecting the patient and posing no risk of infection.

Moreover, the present invention has an additional sinus closing device, which avoids the risk of sinus infection, closing failure and thus saving a second surgery as the sinus can close automatically. In addition, the supplementary sinus flushing device is also convenient for family health care, as it prevents the blocking of the ostomy tube.

The ostomy tube of present invention has equipped with a removable spring, thus the ostomy tube can adopt larger diameter than the prior art, and at the same time it will provide better divert effect, and will not harm the patient when remove the ostomy tube.

Moreover, with scale marks on the ostomy tube in present invention, the ostomy tube can be cut according to the thickness of the patient's abdominal wall, so the drainage distance can be controlled to the shortest, and a better drainage effect can be achieved.

The present invention used a manometer to measure the pressure of the balloon, which guarantees the stable pressure by refilling fluid to the balloon to control the pressure imposed to the intestinal wall by the balloon, thus can play a sufficient blocking effect after the intestinal wall enlarged.

In summary, on the basis of existing ostomy tube, the present invention designs a fixed ostomy tube, as well as various accessories for guiding the ostomy tube out and supplements for avoiding the sinus closing failure after the removal of ostomy tube, thereby overcoming the shortcomings of the prior art.

DESCRIPTION OF THE DRAWING

The following drawings are only for the purpose of description and explanation but not for limitation. Wherein:

FIG. 2 shows a schematic perspective view of the sleeve;

FIG. 3 illustrates the schematic procedure for guiding the ostomy tube out of a patient's abdominal wall via the sleeve;

DESCRIPTION OF PREFERRED EMBODIMENT

Figure 1:
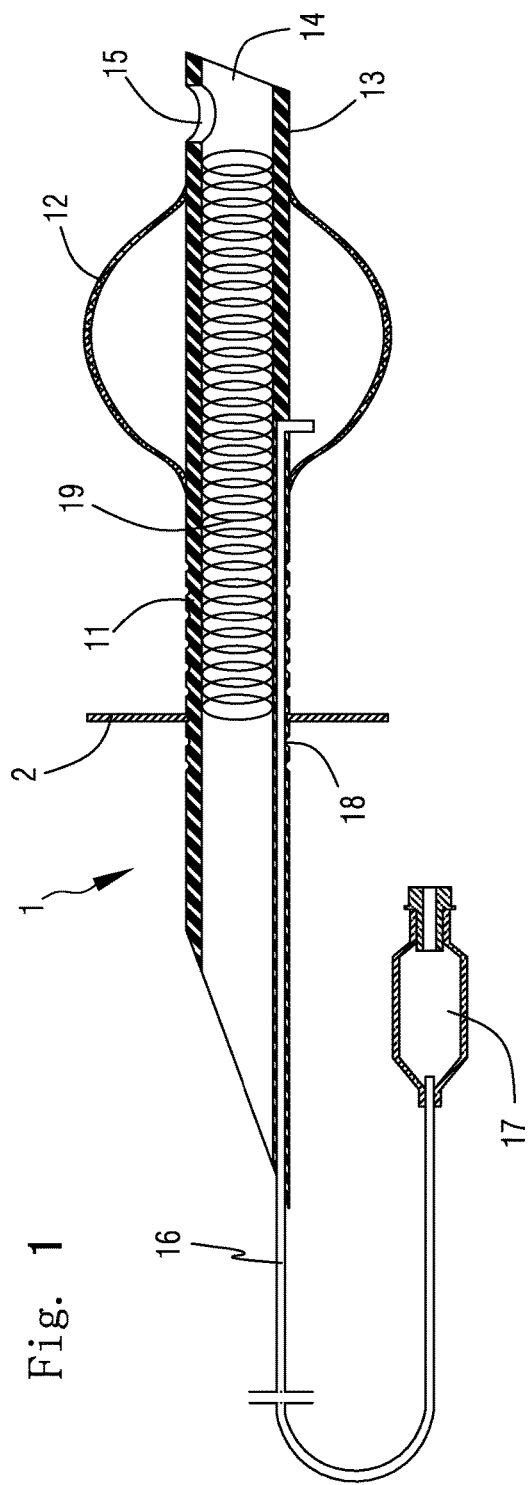
FIG. 1 shows a schematic section view of the ostomy tube of the complete flow diversion intestinal ostomy surgery kit as an embodiment of present invention.

In order that the present invention can be more readily understood, reference will now be made to the accompanying drawings to illustrate the embodiments of the present invention. Wherein, the same components have been marked with the same reference numerals.

As described in the background, the prior ostomy tube adopts small diameter and long distance drainage, the drainage effect of the ostomy tube is poor and cannot achieve perfect protecting effect for the recta anastomosis at the far end. The prior art has no specific wide diameter ostomy tube, however, a wide diameter ostomy tube may lead to the stoma close difficulty and cause risks after removal of the tube.

Therefore, on the basis of the existing tube body, the present invention designs an ostomy tube with specific balloon, and specific structure. And various accessories are supplemented for guiding the ostomy tube out and for avoiding the sinus healing failure after removal of the ostomy tube, which forms the whole complete surgical kit with the ostomy tube. Hereafter, we will illustrate the accessories from the complete flow diversion intestinal ostomy surgery kit of the present invention in detail, with reference to the drawings.

Wherein, the complete flow diversion intestinal ostomy surgery kit of the present invention comprises at least an ostomy tube 1, as shown in FIG. 1, which shows a schematic section view of the ostomy tube 1 of the complete flow diversion intestinal ostomy surgery kit as an embodiment of present invention.

As shown in FIG. 1, ostomy tube 1 comprises a tube body 11 made of synthetic material with length of 15 cm (can be selected according to the thickness of the patient's abdominal wall), inner diameter of 7.5 mm, and outer diameter of 10 mm, with a deformable balloon 12 at its front end. Tube body 11 can be made of soft and thin silica gel. Balloon 12 can be made by a deformable, high compliance and low tension material, such as natural rubber, which has good stretch ability, ensures the safety when the balloon 12 blocks the intestinal channel, and avoids excessive pressure caused by the balloon 12 imposed to the intestinal wall leading the intestinal wall ischemia and necrosis. Balloon 12 has the characters of acid/alkali resistance, 37° C. resistance and digestive fluid resistance, and it can be invariance for 2 months in vivo. Of course, other elastic materials can be used for patients who have rubber allergy.

Balloon 12 of present invention has a diameter of 3.5 cm. Filled with water or gas, balloon 12 will impose pressure to the intestinal wall, when the balloon deforms and extends forward and rear, the pressure decreases and blocks the intestinal canal, which is effective safe in blockage. After tube ileostomy, with the increase peristalsis, the intestinal canal expanses gradually with the pressure generated by matters inside the intestine. The balloon 12 with water filled in can also extend forward and rear because of its sufficient extensibility, which keeps the pressure to the intestinal wall, and delays the blocking duration. The protection period for the tube ileostomy in currently clinical application is about three weeks. We can check the anastomosis three weeks later. The ostomy tube can be removed if the anastomosis heals well. If the anastomosis at the far end has not healed, we can refill water or gas into the balloon 12 to block the intestinal canal to continue divert matters inside of the intestine. Controllability is the most notable characteristic of the present ostomy tube, we can control the divert effect and adequate assurance the anastomotic stoma at the far end closed. Distinguished from the prior ostomy tube for protecting the recta anastomotic stoma, with the help of a sinus closing device, although we use a wide diameter tube body, the sinus can close automatically after removal of the ostomy tube. This is the second characteristic of present ostomy tube.

The said tube body 11 forms a drainage section 13 at the preceding part of the balloon 12, which has an easy insertable oblique drainage port 14, through which matters inside of the intestine can be guided out. On the tube wall of drainage section 13, there is spindle side hole 15 to assistant drainage. When peristalsis, oblique drainage port 14 may be covered by intestinal mucosa, spindle side hole 15 can keep smooth drainage effect. This avoids the intestinal wall early dilation due to poor drainage and high pressure and keeps the protective effect of ostomy tube 1. The slope angle of oblique drainage port 14 is 30-60°, which enlarges the drainage cross-section, meanwhile, when body 11 inserted in, only 0.5 cm incision in intestinal wall is enough for the 1 cm diameter tube. As the smaller the incision is, the incision will heal faster after the tube removed, the lower rate of healing failure will be.

A fine tube 16 is provided within the tube wall of the said tube body 11 or inside the said tube body 11; the front end of the fine tube 16 penetrates the tube wall of the tube body 11 and is in communication with the inner cavity of the balloon 12; the rear end of the fine tube 16 connects a connector 17 for injecting fluid (gas or liquid, such as air or water) into the balloon 12 with a one-way valve; the connector 17 is equipped with a manometer (not shown in Figs.) for measuring the pressure caused by the balloon impressed to the intestinal wall. The one-way valve connected to connector 17 can be any kind of valve with one-way conductive function. To show clearly in figure, the specific structure of the one-way valve has not been specific shown.

Figure 4:
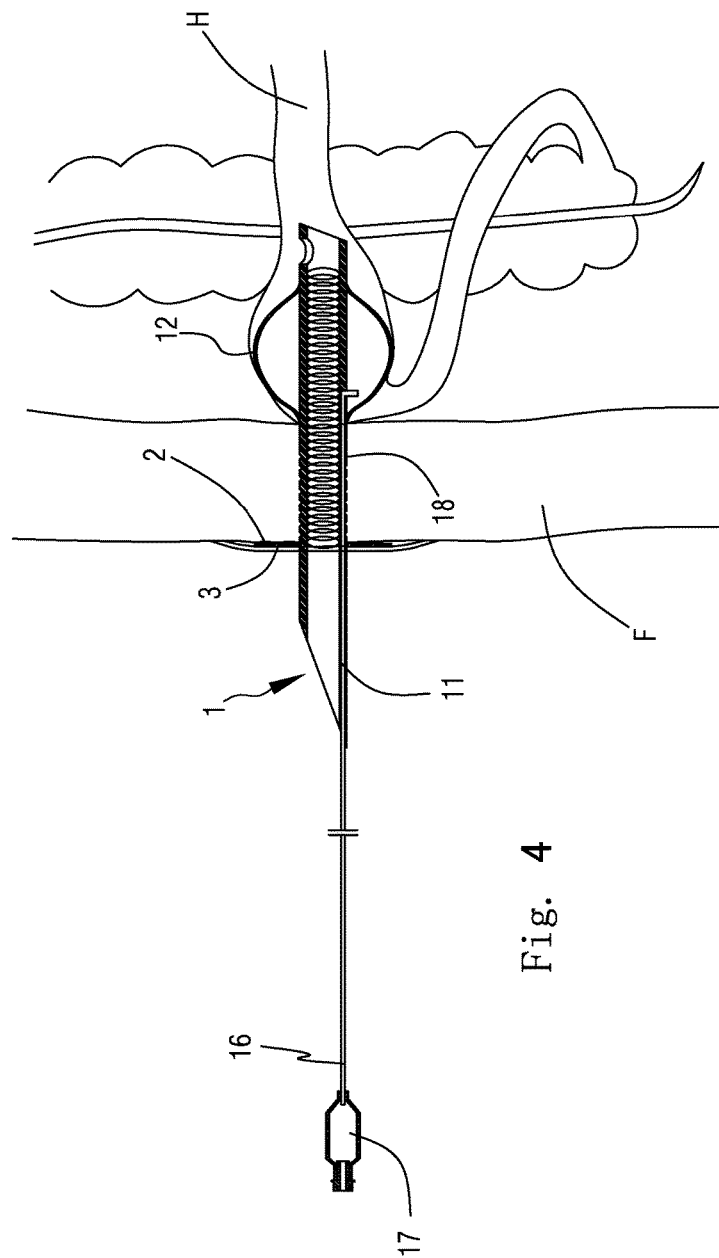
FIG. 4 illustrates the situation that the ring-shaped fixing plate stuck on the outside of the abdominal wall after the ostomy tube guided out from the abdominal wall and the sleeve is removed.

After filled with fluid via the connector 17, the balloon 12 and the intestinal wall form a sealed structure that blocks matters inside of the intestine as shown in FIG. 3-4.

Figure 1A:
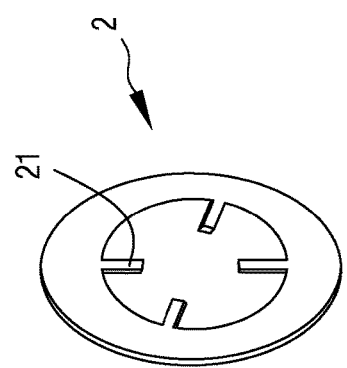
FIG. 1a shows a schematic perspective view of the ring-shaped fixing plate shown in FIG. 1.

Unlike the prior art, the complete flow diversion intestinal ostomy surgery kit of present invention further comprises a ring-shaped fixing plate 2, as shown in FIGS. 1 and 1a, in which FIG. 1a shows the schematic perspective view of the ring-shaped fixing plate 2 shown in FIG. 1. Correspondingly, the exterior tube wall of the tube body 11 is provided with a ring-shaped groove 18; the said ostomy tube 1 is fixedly connected to the abdominal wall of a patient via the ring-shaped fixing plate 2 that matches the ring-shaped groove 18. That is, after the ileostomy operation finished, in order to fix the ostomy tube 1 and avoid it to be dragged back into the abdominal cavity because of the intestinal tract peristalses, the present invention provided a snap structure with ring-shaped fixing plate 2 and ring-shaped groove 18. The tube body 11 of the ostomy tube 1 can be stuck on the outside of the abdominal wall by the ring-shaped fixing plate 2, which avoid the tube body 11 retract to the abdominal cavity. In prior art, the tube body 11 is fixed to the abdominal wall by sutures, which increase the sufferings of patients, and the suture position are easily infected. In present invention, the ring shaped plate 2 and ring-shaped groove 18 form a snap structure without suture, which is easy to operate and brings no risk of infection.

Furthermore, the exterior wall of the tube body 11 has scale marks. Tube body 11 of different length specifications can be selected according to the thickness of the abdominal wall (can be measured during surgery), or it can be cut short to appropriate length with tools like scissors according to the thickness of the abdominal wall in compliance with the scale marks on the tube body 11. Meanwhile, the scale marks on tube body 11 can help locating the ring shape fixing plate 2, to avoid being too loose as to come off or too tight as to cause itch.

Specifically, the ring-shaped fixing plate 2 can just be a simple ring shaped structure. The inner diameter of the ring-shaped fixing plate 2 is slightly smaller than the outer diameter of tube body 11, thus the ring-shaped fixing plate 2 can be stuck in an annulus groove by the way of pressing. Or, as shown in FIG. 1a, the ring-shaped fixing plate 2 can form a structure that the inner ring of the ring-shaped fixing plate can be provided with four jaws 21 extending along the diameter of the ring-shaped fixing plate, the space between the ends of the four jaws 21 is slightly smaller than the outer diameter of the tube body 11, and the ring-shaped fixing plate can also be stuck in the ring-shaped groove 18 by the way of pressing the jaws 21. The structure shown in FIG. 1a has the advantage that these four claws 21 are easy to deform elastically, thus making it easy to get stuck to the exterior tube body 11 and also easy to dismount from the tube body 11. In particular situations, the structure in FIG. 1a can also omit the ring-shaped groove 18 at the exterior tube body 11, only using the friction between the four claws 21 and the tube body 11 to get stuck. Of course, ring-shaped groove 18 can achieve better stuck effect.

Correspondingly, the ring-shaped fixing plate 2 can fix with the abdominal wall by sticking on the upper or inner side of the stoma chassis 3 in two manners. First manner: after the ring shaped fixing plate 2 gets stuck in the ring shaped groove 18, the ring-shaped fixing plate 2 can be adhered to the abdominal wall using adhesive with resist sensibilising on the side of the ring-shape fixing plate 2 facing the abdominal wall. Then a cropped suitable sized stoma chassis (shown in FIG. 4) can be placed on the periphery of the ring-shaped fixing plate 2 to protect the incision, with an ostomy bag adhered to the outside of the stoma chassis for holding the matters inside of the intestine finally. Second manner: after the ostomy tube 1 has been guided out of the abdominal wall, we can adhere the stoma chassis on the abdominal wall, and then stick the ring-shaped fixing plate into the groove of the ostomy tube, with the underside of the ring-shaped fixing plate 2 adhered with the stoma chassis. As the stoma chassis is a commonly used adhere means in surgical operations, whose structure is well known in the art and thus will not be described here in detail.

In addition, as described above, the ring-shaped fixing plate 2 can be detachable so it can be replaced when changing the stoma chassis.

When the ring-shaped fixing plate 2 is fixed, the skin around is under uniform pressure to avoid unwell such as dermatitis caused by uneven pressure.

In another specific embodiment of the present invention, the interior of the said tube body 11 has a removable spring bracket 19, as shown in FIG. 1. With spring bracket 19 support, the tube body 11 which comes through abdominal wall won't be extruded, thus ensuring the smooth drainage effect of ostomy tube 1. Before removal of ostomy tube 1, spring bracket 19 can be pulled out of the tube body 11. Without spring bracket support from inside the tube which is made of composite material, the tube body 11 will be soft and thin, and can be pulled out of the intestine easily without intestinal injury.

Furthermore, the complete flow diversion intestinal ostomy surgery kit can further comprise a sleeve 4 placed at the rear end of the tube body 11 matched therewith, for guiding the tube body 11 out of the patient's abdominal wall, as shown in FIG. 2, which shows a schematic perspective view of the sleeve 4. The front side of sleeve 4 is a slope, making it pass through the abdominal wall F easily. The connector 17 at the end of ostomy tube 1 is too big in size to be pulled out, so sleeve 4 is easy for operation and avoid intestine injury, as shown in FIG. 3-4.

Here we describe the operational procedure of the complete flow diversion intestinal ostomy surgery kit in detail below with reference to FIG. 3-4. FIG. 3 shows the procedure of the ostomy tube 1 pulled out from the abdominal wall F through the sleeve 4. FIG. 4 shows after ostomy tube 1 is pulled out from abdominal wall F, sleeve 4 is removed, and ostomy tube 1 is fixed outside abdominal wall F with ring shaped fixing plate 2.

During a rectal cancer surgery, in order to avoid intestinal matters to reach rectum, we process enterostomy to pull intestinal matters out of body after rectal cancer resection. Without intestinal matter contamination, rectal incision won't be infected.

We process purse-string suture in 1.0 and 1.5 cm diameter with absorbable suture at the end of ileum, 15 cm away from ileocecal valve (figure not shown). Then we make a small incision in the central part of purse-string suture with electrotome and place ostomy tube 1 into ileum H tipsily. Tie the purse-string suture until the whole balloon 12 is inside. Then inject water at connector 17 and keep the pressure to intestinal wall between 30-40 cmHg. Make a 1 cm incision at abdominal wall F, and work sleeve 4 into abdominal wall F. At last, ostomy tube 1 is guided out of abdominal wall F through sleeve 4.

Later, as shown in FIG. 4, remove sleeve 4, suture ileum H and abdominal wall F together around ostomy tube 1 with absorbable surgical suture inside abdominal cavity.

Then put ring-shaped fixing plate 2 above tube body 11 and stick the tube body into ring-shaped groove 18. There is adhesive phase with anti-allergy substances on the ring-shaped groove at the side forward abdominal wall 18 for stick to abdominal wall. Place stoma chassis 3 out of ring-shaped fixing plate 2 and put pouching out of stoma chassis 3 for holding matters inside of the intestine. The design of ring-shaped fixing plate 2, can avoid the retraction of ostomy tube 1, and protect the skin from contamination by manure and dermatitis.

After the surgery, we should take care to monitor the balloon 12 pressure. As the dilation of intestinal canal, the block effect of balloon 12 will decrease gradually. If there is leak at remote side of rectal anastomosis, inject water into balloon 12 to keep it closure, and then extend its protective period.

Three weeks after rectal cancer surgery, we check healing condition of the remote rectal anastomosis. If it heals well, ostomy tube 1 can be removed as follows: evacuate balloon 12, pull elastic spring 19 out of tube body 11; as tube body turns soft and thin, ostomy tube 1 can be removed without injury to intestinal wall. As ostomy tube 1 is tightly sutured with ileum, the removal of ostomy tube 1 may cause injury of intestinal wall or bleeding or even perforation. In order to avoid these risks, the said tube 1 is made of soft material and keep deformable with elastic spring's support, thus guarantee the drainage effect. After removal of elastic spring 19, tube 1 will be thin by abdominal wall extrusion without spring bracket 19 support. Then it is safe to remove the ostomy tube without injury to intestine.

After ostomy tube 1 removed, there is a sinus between abdominal wall F and ileum H. As sinus healing takes time, if the abdominal wall heals before sinus heals, intestinal matters will remain inside the sinus canal and cause repeated infection.

Figure 5:
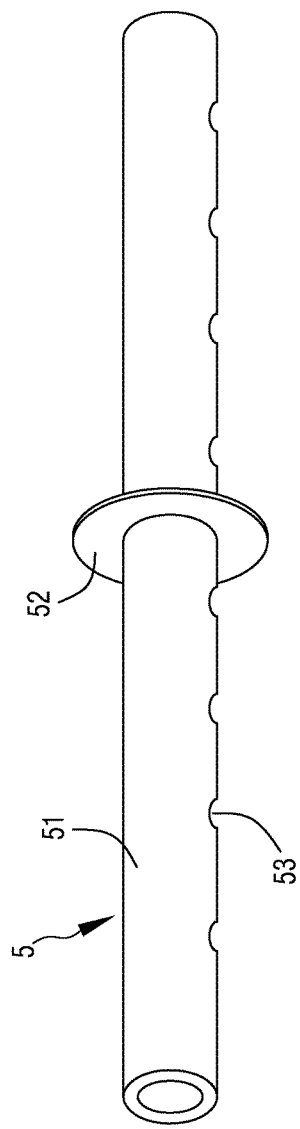
FIG. 5 shows a schematic perspective view of the sinus closing device.
Figure 6:
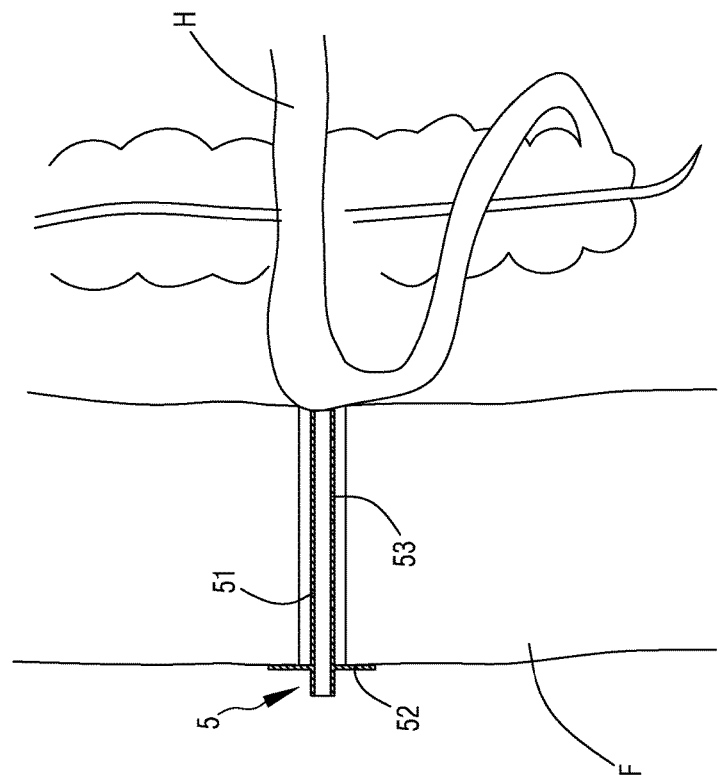
FIG. 6 illustrates a schematic operation view of the sinus closing device.

To avoid this situation above, this invention compromises a sinus closing device 5 as shown in FIG. 5-6. FIG. 5 shows a schematic perspective view of the sinus closing device, FIG. 6 illustrates a schematic operation view of the sinus closing device. As shown in FIG. 5, sinus closing device 5 is comprised of a drainage tube 51 and an outer fixing ring 52, which can stick to stoma chassis and play a supporting role. There are scales on exterior of drainage tube 51. The position where the outer fixing ring located 52 is marked with zero scale, the scale marks on the drainage tube on both sides of the said outer fixing ring are extended with millimeters. The big and strong structure combined by drainage tube 51 and outer fixing ring 52 avoids submarining. Moreover, it is easy to manufacture and low in cost.

As shown in FIG. 5-6, sinus closing device 5 can help sinus close and avoid a second surgery due to sinus closing failure. After removal of ostomy tube 1, the length of the said drainage tube 51 can be modified by scissors, according to the depth of sinus (measured during surgery) and the scales at drainage tube 51. As the in FIG. 6, after drainage tube 51 cut, the length of the said drainage tube 51 is just fit the distance from ileum H to abdominal wall F, leaving outer fixing ring clinging to abdominal wall F tightly. Moreover, 5 mm of drainage tube 51 out of abdominal wall F is enough.

As shown in FIG. 5, outer fixing ring 52 is in the middle of drainage tube 51. The said drainage tube can be cut at both ends to insert into the sinus during surgery. Even the surgeon cut the tube of a wrong length; they can choose the other end to operate again. It is another advantage to set the outer fixing plate location at scale zero.

As ileum H is sutured with abdominal F, the sinus is unmovable. Even if it is a little tight when drainage tube 51 reaches ileum H, it won't be pull ileum H away from abdominal wall F. With scales on the drainage tube 51, the said drainage tube won't be too long to insert into ileum so as to delay intestine healing.

After the drainage tube 51 inserted into sinus, it is fixed outside the abdominal wall by outer fixing plate 52. As the outer diameter of drainage tube is only 3 mm, the sinus heals from 10 mm to 3 mm slowly, and drains smoothly, which is good for sinus healing.

In this invention, the key point for sinus close is to keep drainage smooth. Outer fixing plate 52 can be stuck to stoma chassis, drainage tube 51 is silica gel and 3 mm in inner diameter. There are multiple side holes 53 along the said drainage tube 51 uniformly. The scales outside the drainage tube 51 can measure the depth of sinus and as a reference to prune its length, let the front end of the drainage tube reach the bottom of sinus, not into ileum, which helps sinus healing, keeps smooth drainage, avoids dead space and helps sinus healing automatically, thus avoid repeated infection and a 2nd surgery.

In this invention, sinus closing device 5 is inserted into sinus, the tissue inside the sinus migrates and close the inner side of sinus. The fluid exudating during healing and intestinal matters can be guided out of the body, from the outer side of drainage tube 51 to inner side of the tube by going through the side holes 53. As a result of smooth drainage, fluid is avoided to accumulate inside the sinus and cause infection, thereby sinus heals gradually. When sinus forms, drainage tube 51 is removed and the intestinal matters can be drainage out through sinus, which avoids repeated infection caused by intestinal matters accumulation.

In this invention, as the outer diameter of ostomy tube is 1 cm which is different from prior ones, there are problems such as difficulty in sinus close or repeated infection, even a 2nd surgery in clinical use. In order to make the stoma close automatically without a 2nd surgery, a specific sinus closing device 5 is designed. With the scales on drainage tube 51, we guarantee the sinus close favorably. Drainage tube 51 is fixed to stoma chassis with outer fixing ring 52, which is easy to operate and suitable for wide aperture ostomy. This proposal can keep drainage smooth, pull the tube out gradually, avoid dead space, help sinus close automatically and avoid a reduction surgery.

Figure 7:
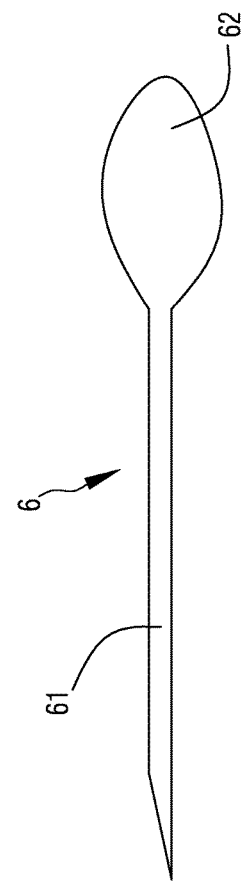
FIG. 7 shows a schematic view of the sinus flushing device.

Moreover, the complete flow diversion intestinal ostomy surgery kit in this invention comprises a sinus flushing device 6 as shown in FIG. 7, which is a schematic perspective view of the sinus flushing device. The said sinus flushing device includes a scaled flushing tube 61 and an aurilave 62. Although the inner diameter of tube 11 is 7.5 mm in this invention, which can guarantee regular drainage, if patient is on an inappropriate diet with a lot residue such as vegetables or fruits with seeds, the tube body 11 will be obstructed. Also, if some patients whose intestinal fluid is very thick, tube body 11 will be obstructed too. With the flushing device consisting of a flushing tube 61 and an aurilave 62, water can be flushed into tube body 11 by patient at home, thus avoid readmission.

In summary, on the basis of existing ostomy tube, the present invention designs a fixed ostomy tube, and various accessories are supplemented for guiding the ostomy tube out and for avoiding the sinus healing failure after the removal of ostomy tube, thereby overcoming the shortcomings of the prior art.

The skilled person in the art should understand that, although the present invention has been described with multiple embodiments, each embodiment does not include only one independent technical solution. It is only for the purpose of clarity to describe like that, the person in the art should understand the specification as a whole and the technical solutions in all embodiments can be inter combined with each other to form the protection scope of the present invention.

Whilst the above description has been given by way of illustrative examples of the present invention, but it is not for limitation of the scope of the invention. Variations and modifications thereto will be apparent to those skilled in the art without departing from the broad ambit and scope of the invention as herein set forth in the following claims.

The invention claimed is:

1. A flow diversion intestinal ostomy surgery kit, comprising:
    at least an ostomy tube, said ostomy tube comprising: a tube body; near the front end of the tube body a deformable balloon; said tube body forming a drainage section at a preceding part of the balloon; a fine tube is provided within a tube wall of said tube body or inside said tube body; a front end of the fine tube penetrates the tube wall of said tube body and is in communication with an inner cavity of the balloon; a rear end of the fine tube connects a connector for injecting fluid into the balloon with a one-way valve; said connector is equipped with a manometer for measuring pressure caused by the balloon impressed to the intestinal wall; said balloon and an intestinal wall form a sealed structure that blocks matters inside of an intestine after filled with fluid via said connector; there is a drainage port at the drainage section for guiding matters inside of the intestine out by said tube body;
    wherein said flow diversion intestinal ostomy surgery kit further comprises a ring-shaped fixing plate; an exterior wall of the tube body is provided with a ring-shaped groove; said ostomy tube is fixedly connected to an abdominal wall of a patient via the ring-shaped fixing plate that matches the ring-shaped groove;
    wherein an inner ring of said ring-shaped fixing plate is provided with four jaws configured to touch the ostomy tube body and extending along a diameter of said ring-shaped fixing plate, said jaws provided in pairs with an end of each jaw configured to be directly across the ostomy tube body from another jaw end, a space between ends of the four jaws is slightly smaller than an outer diameter of said tube body, said ring-shaped fixing plate stuck in said ring-shaped groove by way of pressing said jaws.

2. The flow diversion intestinal ostomy surgery kit according to claim 1, wherein said ring-shaped fixing plate is stuck on the upper or inner side of the stoma chassis.

3. The flow diversion intestinal ostomy surgery kit according to claim 1, wherein inside said tube body is a pullable and pushable spring bracket.

4. The flow diversion intestinal ostomy surgery kit according to claim 1, wherein said flow diversion intestinal ostomy surgery kit further comprises a sleeve placed at a rear end of the tube body matched therewith, for guiding the tube body out of the patient's abdominal wall.

5. The flow diversion intestinal ostomy surgery kit according to claim 1, wherein said flow diversion intestinal ostomy surgery kit further comprises a sinus closing device, said sinus closing device comprises a drainage tube and an outer fixing ring integrated therewith, an outside wall of the drainage tube has scale marks.

6. The flow diversion intestinal ostomy surgery kit according to claim 5, wherein a position where the outer fixing ring located is marked with a zero scale, the zero scale having marks on the drainage tube on both sides of said outer fixing ring that are marked in millimeters.

7. The flow diversion intestinal ostomy surgery kit according to claim 6, wherein along a longitudinal direction of the said drainage tube are provided multiple holes distributed uniformly through a side of said drainage tube.

8. The flow diversion intestinal ostomy surgery kit according to claim 3, wherein said complete flow diversion intestinal ostomy surgery kit further comprises a sinus flushing device, which comprises a flushing tube with scale marks, a top side of said flushing tube has an aurilave.

* * * * *